United States Patent [19]

Nissen

[11] Patent Number: 5,360,613
[45] Date of Patent: Nov. 1, 1994

[54] METHOD OF REDUCING BLOOD LEVELS OF TOTAL CHOLESTEROL AND LOW-DENSITY LIPOPROTEIN CHOLESTEROL

[75] Inventor: Steven L. Nissen, Ames, Iowa

[73] Assignee: Iowa State University Research Foundation, Inc., Ames, Iowa

[21] Appl. No.: 136,688

[22] Filed: Oct. 14, 1993

Related U.S. Application Data

[63] Continuation-in-part of Ser. No. 946,404, Sep. 16, 1992, abandoned.

[51] Int. Cl.$^5$ ............................................. A61K 47/00
[52] U.S. Cl. .................................... 424/439; 424/451; 424/464; 514/824; 514/838; 514/893
[58] Field of Search .................. 424/451, 439, 464; 514/824, 838, 893, 557

[56] References Cited

U.S. PATENT DOCUMENTS

| | | | |
|---|---|---|---|
| 3,629,449 | 12/1971 | Siddiqi et al. | 424/317 |
| 4,760,090 | 7/1988 | Nissen | 514/557 |
| 4,764,531 | 8/1988 | Nissen | 514/557 |
| 4,992,470 | 2/1991 | Nissen | 514/578 |
| 5,028,440 | 7/1991 | Nissen | 426/2 |
| 5,087,472 | 2/1992 | Nissen | 426/623 |

OTHER PUBLICATIONS

Tanaka et al., *Biochim. Biosphys. Acta.* 152:638–641 (1968).
Landass, *Clin. Chim, Acta.* 64:143–154 (1975).
Sabourin, *Metabolism* 32:160–164 (1983).
Mock et al., *J. Lab. Clin. Med.* pp. 240–247 (1988).
Van Koevering et al., *Am. J. Physiol.* 262:E27–E31 (1992).
Adamson et al., *Biochem. Biophys. Acta.* 23:4720479 (1957).
Yousufzai et al., *Lipids,* 11:526–529 (1975).
Lupien et al., *J. Clin. Pharm.* 19:120–126 (1079).
Gey et al., *Helvetica Chim. Acta.,* 40:2354–2368 (1957).
Coffman et al., *J. Am. Chem. Soc.,* 80:2882–2997 (1958).

*Primary Examiner*—D. Gabrielle Phelan
*Attorney, Agent, or Firm*—Tilton, Fallon, Lungmus & Chestnut

[57] ABSTRACT

Patients with elevated blood levels of low-density lipoprotein (LDL) and total cholesterol are treated by administering β-hydroxy-β-methylbutyric acid (HMB) to reduce the patient's blood level of LDL and total cholesterol. HMB can be safely administered orally to humans in amounts that will significantly reduce blood levels of total cholesterol and LDL.

6 Claims, No Drawings

METHOD OF REDUCING BLOOD LEVELS OF TOTAL CHOLESTEROL AND LOW-DENSITY LIPOPROTEIN CHOLESTEROL

RELATED APPLICATION

This application is a continuation-in-part of copending application Ser. No. 07/946,404, filed Sep. 16, 1992, now abandoned.

FIELD OF INVENTION

This invention relates to methods of reducing blood levels of cholesterol, and more particularly the reduction of low-density lipoprotein (LDL) cholesterol. The invention involves oral administration of a therapeutic agent for decreasing plasma cholesterol concentration.

BACKGROUND OF INVENTION

It is generally accepted that elevated blood cholesterol is a causative factor of coronary heart disease. Moreover, it is recognized that high blood levels of the form of cholesterol known as low-density lipoprotein (LDL) can contribute to cardiovascular disease. Guidelines have been established to indicate to doctors when patients should be considered at risk. Desirable is less than 200 mg/dl, borderline is 200 to 239 and high is greater than 140 mg/dl Schueker et al., *Arch. Inter. Med.* (1991) 151:666–673. If total cholesterol is greater than 240 mg/dl and/or LDH is above 160 mg/dl, therapeutic treatment may be needed. [See Goodman, *Amer. J. Med.*, 90:2A–32S to 2A–35S (1991).]

The development of the present invention began with experiments conducted at Iowa State University, Ames, Iowa, U.S.A. in which metabolic products of leucine were feed to domestic animals. As described in U.S. Pat. No. 4,760,090 of Steven L. Nissen, it was found that ketoisocaproic acid (KIC) can be feed to cattle and sheep for enhancement of growth and feed efficiency. It was observed that during such KIC feeding there was some reduction in plasma cholesterol, and also in the deposit of cholesterol in the meat. (See 4,760,090, col. 5–6, Table B.)

In another application of KIC feeding, egg production of laying chickens was increased, as described in U.S. Pat. No. 4,764,531 of Steven L. Nissen. It was found that the eggs of KIC feed chickens had reduced yolk cholesterol (4,764,531, col. 4, Table B).

In later experiments carried out by Dr. Steven L. Nissen at Iowa State University, $\beta$-hydroxy-$\beta$-methylbutyric acid (HMB) was fed to domestic animals. The effects obtained were different than with KIC. Metabolically, KIC and HMB are not equivalents. KIC is the only metabolic product of leucine, while HMB is a minor product of KIC metabolism.

Leucine is either used for protein synthesis in the body or is converted directly to KIC. In the mitochondria KIC is decarboxylated to isovalarylCoA and then further metabolized to ketone bodies. In certain disease conditions, such as isovalaric acidemia, an alternate oxidative pathway for KIC has been observed, which appears to produce $\beta$-hydroxy-$\beta$-methylbutyrate (HMB). In atypical cases, such as a genetic absence of the dehydrogenase enzyme, there is evidence that HMB can accumulate in the urine: Tanaka, et al. *Biochim. Biosphys. Acta.* 152:638–641 (1968). Also, in acidosis conditions, HMB levels can be increased in urine: Landass, *Clin. Chim. Acta.* 64:143–154 (1975). This presumably occurs by oxidation of KIC to HMB by the enzyme $\alpha$ketoiscaproate oxygenase (Sabourin, *Metabolism* (1983) 32:160–164). Increased urine HMB can also occur in cases of biotin deficiency (Mock, *J. Lab. Clin. Med.* (1988) 240–247). The only evidence for normal HMB production is in lambs and pigs, Vankowering and Nissen, *Am. J. Physiol.* (1992) 262:E27–E31. In this study it was estimated that <10% of leucine metabolic is via HMB production.

The differing activities of HMB as fed to domestic animals provided the basis for additional patents of Steven L. Nissen. His U.S. Pat. No. 4,992,470 discloses the administration of HMB for enhancing the immune response of mammals and as an ingredient in the raising of meat producing animals (e.g. ruminants and poultry) to increase lean tissue development. (See U.S. Pat. Nos., 5,087,472 and 5,028,440 of Steven L. Nissen.)

There has been a scientific effort to determine how cholesterol is synthesized in the bodies of mammals. It was known that acetate can be synthesized into cholesterol. Research investigations in the 1940's and 1950's concentrated on experiments with organic acids which also incorporated acetate and whose tracers could be incorporated into cholesterol. A small group or organic acids appeared to meet these qualifications. This included $\beta$-hydroxy-$\beta$-methylglutarate (HMG), $\beta$-hydroxy-$\beta$-methylbutyrate (3-hydroxy isovalarate), $\beta$-$\beta$-dimethylacrylate (DMA), isovalarate, and $\beta$-methyl-gluconate ($\beta$MG). 14C from 14C-acetate can be detected in all these compounds. Today it is thought that HMG-COA is the obligatory precursor to cholesterol, and the other compounds referred to herein are somehow incorporated in cholesterol by interconversion with HMG. (Adamson et al. 1957, *Biochem. Biophys. Acta*, 23: 472–479.) Thus, although there is a biochemical relationship between HMG and HMB, it is not clear if there is any relationship between the compounds regarding effects on cholesterol metabolism.

Experiments demonstrated that feeding HMG to rats could decrease total serum cholesterol by up to 20%. Effects on LDL cholesterol were not reported (Yousufzai et al., *Lipids*, 11:526–529).

Only limited human studies have been carried out with HMG. One study did measure the effect of HMB on subjects with familial hypercholesterolemia, and LDL was measured. A modest decrease in total cholesterol and LDL cholesterol was reported. (Lupien et al., *J. Clin. Pharm.*, 19:120–126, 1979.)

After 8 weeks of being fed 3 grams of HMG daily, total cholesterol decreased from 404 to 353 mg % (−13%) and LDL decreased from 333 to 307 mg % (−8%). HDL cholesterol decreased approximately 35%. Thus, HMB appears to act differently from HMG in humans in that the effect is more pronounced and results in a specific decrease in LDL cholesterol but not in HDL cholesterol.

U.S. Pat. No. 3,629,449 claims that oral HMG can reduce serum cholesterol (total) and blood lipids (triglycerides) in warm-blooded animals.

Only one study is known where HMB was fed to animals, and an index of cholesterol metabolism measured: Gey et al., *Helvetica Chim. Acta*, 40:2354–2368 (1957). In that study HMB was fed to rats at a rate of 0.5 g/kg body weight for 2 and 4 days. At the end of the study, cholesterol synthesis was measured by removing the liver which was incubated in slices with 14C acetate. Cholesterol was isolated following the incubation and radioactivity quantitated. It was found that HMB had not significantly lowered the rate of acetate incorporation into cholesterol by the rat liver as compared to controls. In the same paper, an in vitro interaction of HMB and acetate incorporation was assessed. When HMB was added to the media at very high concentrations, it was found that there was no significant inhibition of acetate incorporation compared to the control values.

SUMMARY OF INVENTION

This invention is based on the development of scientific evidence that β-hydroxy-β-methylbutyric acid (HMB) can be used as an effective anti-cholesterol agent. In particular, the scientific data developed to date indicates that HMB can be safely administered orally to humans in amounts that will significantly reduce blood levels of total cholesterol, and, even more importantly, blood levels of low-density lipoprotein (LDL) cholesterol. HMB may be produced in small amounts from the amino acid leucine provided by protein-containing foods. However, administration of leucine or its metabolic conversion product ketoisocaproic acid (KIC) have not been reported to be effective anti-cholesterol agent in humans.

DETAILED DESCRIPTION

The compound used for practicing the present invention is β-hydroxy-β-methylbutyric acid (HMB), or edible derivatives thereof which directly convert in the body to HMB. The free acid compound is also called β-hydroxy-isovaleric acid. It has the following structure:

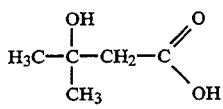

While HMB can be administered in its free acid form, it is preferred to administer an edible form of HMB which is a salt, ester, or lactone. The calcium salt is preferred because it is less hydroscopic than the sodium or potassium salts, but those salts can also be used, depending on the mode of oral administration. Esters of HMB such as particularly the methyl or ethyl esters are also suitable. Such esters are rapidly converted in the body to the free acid form of HMB. For administration as a lactone, the compound isovalaryl lactone can be used. This compound and similar lactones are rapidly converted in the body to free acid HMB.

The free acid form can be more specifically designated as "HMB acid". The salt forms, such as the calcium, sodium, potassium or magnesium salts, as "Ca-HMB", "Na-HMB", "K-HMB", and Mg-HMB. Correspondingly, the esters can be designated "HMB-methyl ester", "HMB-ethyl ester", etc. The lactone can be designated "HMB-lactone". HMB has no stero-isomers and accordingly does not exist in L or D forms.

HMB is not currently commercially available. However, procedures are known for synthesizing this compound from commercially available starting materials. For example, HMB can be synthesized by oxidation of diacetone alcohol (4-hydroxy-4-methyl-2-pentanone). One suitable procedure is described by Coffman, et al., *J. Am. Chem. Soc.*, 80:2882-2887, at 2885 (1958). As there described, β-hydroxy-isovaleric acid (HMB) is synthesized by an alkaline sodium hypochlorite oxidation of diacetone alcohol. The product is recovered in free acid form, which can be converted to the desired salt. For example, HMB can be prepared as its calcium salt (Ca-HMB) by a similar procedure to that of Coffman, et al. in which the HMB acid obtained is neutralized with calcium hydroxide, and recovered by crystallization from an aqueous ethanol solution. For example, a 95% ethanol solution can be used with the Ca-HMB at about a 10% concentration.

Since Ca-HMB is a preferred form for administering HMB, the dosage amount of HMB can be expressed in terms of corresponding mole amount of Ca-HMB. The dosage range within which HMB can be usefully administered is from 0.01 to 0.2 grams HMB (Ca-HMB basis) per kilogram of body weight per 24 hours. For adults, assuming body weights of from about 100 to 200 lbs., the dosage amount of HMB (Ca-HMB basis) can range from 0.5 to 10 grams per patient per 24 hours. For most adults, on the basis of present data, it is believed that the optimum dosage is in the range from 2 to 6 grams of HMB (Ca-HMB) per 24 hours.

Ca-HMB and other forms of HMB as described above can be processed as fine powders which can be filled into capsules, or combined with tableting diluents, such as lactose, and compressed into tablets of predetermined dose amounts. No special mode of administration is needed. One preferred mode is to package the Ca-HMB in water-soluble capsules, such as gelatin capsules. Each capsule may contain as the predetermined amount of the Ca-HMB 0.5, 1, or 2 grams. Multiple doses per day are desirable, and therefore smaller dose sizes are believed preferable. However, if desired, larger doses in capsules or tablets can be prepared, such as 4 grams per capsule or tablet. A suitable regiment for oral administration to adults consists of one tablet or capsule one to four times per 24 hours. If taken once per day, it is preferred it be consumed before bedtime.

The experimental basis of the present invention and the results that can be obtained can be more fully appreciated and understood from the following examples.

EXAMPLE I

A preliminary experiment was carried out using hamsters as the test animal and Na-HMB as the therapeutic agent. The experimental details and the results obtained are described as follows.

Pregnant Female hamsters were housed and allowed to give birth. At three weeks of age, litters were subdivided into pairs within a sex. The pairs of hamsters were then assigned randomly a purified diet based on casein and cornstarch with either contained 0.1% NaCl (control) or one containing 0.1% Na-HMB (HMB). They were maintained on this diet for 6 weeks at which time they were killed by decapitation and blood collected into EDTA containing tubes. Blood was separated by centrifugation and plasma collected. The unfrozen plasma was treated with an LDL precipitating agent, centrifuged and the supernatant collected. The whole plasma and supernatant were assayed for cholesterol by an enzymatic method. Plasma cholesterol estimated total cholesterol while the supernatant represented HDL cholesterol. LDL cholesterol was estimated by the formula: LDL-Cholesterol=(Total cholesterol)-(HDL cholesterol)-(triglycerides X 0.2). Total triglycerides in plasma were estimated by an enzymatic assay. The results are summarized in Table A.

TABLE A

CHOLESTEROL (mg %)

| Sex | Diet | No. | Total | HDL | LDL | HDL/LDL | Triglycerides mg % |
|---|---|---|---|---|---|---|---|
| Females | Control | 8 | 237 | 125 | 64 | .51 | 240 |
| Females | HMB | 8 | 228 | 132 | 53 | .41 | 212 |
| % Change | | | −4% | +5% | −17% | −20% | −11% |
| Males | Control | 7 | 217 | 111 | 59 | .53 | 232 |
| Males | HMB | 7 | 208 | 118 | 45 | .38 | 226 |
| % Change | | | −4% | +5% | −24% | −28% | −2% |

The foregoing data indicates that HMB can markedly lower LDL cholesterol in hamsters. The data also suggests a trend to increase HDL cholesterol, and that the ratio of LDL/HDL is positively affected.

EXAMPLE II

In view of the encouraging results of Example I, a large mammal study was carried out with lambs. HMB was administered in the form of Ca-HMB.

Animals and Feeding

Cross-bred lambs were obtained from a research flock. Males were selected from a pool of 108 rams while females were selected from a pool of 63 females. Selection was based on weight range, breed and previous performance. Breeding consisted of Dorset, Polypay and Suffold crosses. Males were divided into 5 weight blocks and females into 3 weight blocks. The two heaviest male blocks contained 27 lambs, allotted to 3 pens. All other blocks contained 18 lambs, allotted to 2 pens. Animals were weighed on consecutive days prior to starting the experiment. All animals were shorn 100 days into the experiment. The animals were housed in a single confinement unit with uniform pens. The feeders were concrete bunks with water supplied by several nipple waterers per pen. Dirt flooring was bedded with oat straw when necessary. Weight blocks were placed in adjacent pens with treatment randomly assigned to the blocks. The ration was complete in all nutrients for growing sheep. The diet was formulated to contain protein in excess of the normal requirement in an effort to assure that protein was not a limiting factor for any growth response. The feeding schedule consisted of two feedings per day with the amount controlled so that the animals had eaten all the feed from the previous feeding before being fed again. Also with the feed allotment, a top-dressing of 20 g of either a control premix containing HMB was added at the equivalent of 0.5 gram per animal per day and 1.5 gram per animal per day.

Preparation of HMB

Ca-HMB was prepared by minor modification of the method of Coffman, et al. *J. Am. Chem. Soc.*, 80:2882-2887 (1958). More specifically, the crude HMB was first purified by distillation under vacuum, neutralized with Ca(OH)$_2$, and finally the calcium salt crystallization three times from 95% ethanol. The product was then air-dried and fine-ground. Each batch was given a lot number and the purity assessed by high performance liquid chromatography. A single peak was measured when HMB was chromatographed on a C18 column and eluted with 0.01M phosphate buffer, pH 7.0. Also nuclear magnetic resonance was performed. This indicated only two peaks which corresponded to the methyl hydrogens and the CH$_2$ hydrogens.

Analytical Procedures

Blood was collected from each animal. The plasma was analyzed for cholesterol using an Abbott Spectrum Diagnostic system. In all cases the pen means were used for analysis of variance. The general linear models procedure of the Statistical Analysis System (SAS) was used to analyze the model. A linear effect of HMB level was evaluated.

Results

The studies indicated that oral consumption of HMB decreased plasma cholesterol. The relevant data is summarized below in Table B.

TABLE B

Daily Consumption of HMB

| | Control | 0.5 g HMB | 1.5 g HMB | Linear Effect |
|---|---|---|---|---|
| No. Pens | 8 | 8 | 2 | |
| Total animals | 71 | 71 | 17 | |
| Plasma cholesterol | 54.3 | 51.3 | 48.1 | 0.05 |

EXAMPLE III

A further large mammal study was carried out with pigs. Pigs comprise test animals which are more similar in certain respects to humans than ruminants.

Feeding Regimens

| Diet | Composition | Daily Dose | Dose/kg body wt. |
|---|---|---|---|
| Control: | 60 g. of calcium carbonate per 227 kg of diet | 0 | 0 |
| 0.01% HMB | 22 g of calcium HMB per 227 kg of diet | 120 mg/day | 1.5 mg/kg |
| 0.05% HMB | 113 g of calcium HMB per 227 kg of diet | 1000 mg/day | 12.5 mg/kg |
| 0.05% KIC | 113 g of calcium KIC per 227 kg of diet | 1000 mg/day | 80 mg/kg |

The pigs were housed in pens of two animals each and were allowed ad libitum access to food and water. Pigs were approximately 160 lbs. at the start of the experiment and were 240 lbs. at the end. All pigs were castrate males. At day 28 and day 43 of the experiment blood was collected from the anterior vena cava by venipuncture. Blood was collected into EDTA containing tubes, centrifuged and frozen until analyzed. At approximately 100 days of the experiment half of the animals (32) were slaughtered, and at 120 days the remaining 32 animals were slaughtered. At the time of slaughter the abdominal aorta was dissected out and external fat removed. The aorta was then split lengthwise and ½ fixed in formaldehyde for 48 hours. At this time aortas were removed, stretched over a 6 inch stick, washed in ethanol and stained with a lipid stain for 2 hours. After a 1 hour wash aortas were blotted and examined. All the aortas from a group were laid out on a white bench and arranged in order from least sever to most sever. The least sever had no dark red streaks on the aorta or around the small vertebral vessels leaving the aorta. The most sever lesions had multiple streaks in the middle of the aorta and dark red deposits in turbulent areas such as the branching of vessels from the aorta. The ordered aortas were then assigned a consecutive decimal number. The first (least severe) was assigned 0 and the most severe was assigned 3.2 Plasma cholesterol and triglycerides were measured by an enzyme-colorimetric assay (Sigma).

Data Analysis and Results statistical analysis was accomplished by the general linear model procedure of the Statistical Analysis System (SAS). The model included the main effects of treatment and pen number. T-tests were conducted from the ANOVA standard error, to compare the HMB treatments to the control. The feeding of HMB to swine indicated that cholesterol metabolism is altered by chronic feeding of HMB. HMB-fed pigs had lower deposits of fat in the aorta. It appeared that HMB can partially prevent the formation of pre-atherosclerotic lesions. No effect of KIC was noted relative to any parameter. The data is summarized below in Table C.

TABLE C

| Variable | Dietary HBM Cont. | .01% | .05% | KIC .05% | Statistical Comparison C vs. .01% | C vs. .05% | C vs. KIC |
|---|---|---|---|---|---|---|---|
| Aorta Streaking | 1.87 | 1.23 | 1.18 | 1.48 | .12 | .06 | ns |
| Plasma Cholesterol (mg %) | 135 | 120 | 118 | 139 | .14 | .05 | ns |
| Plasma Triglycerides (mg %) | 107 | 105 | 109 | 106 | ns | ns | ns |

EXAMPLE IV

In view of the findings of the foregoing examples, a human study was carried out. HMB was administered at comparable doses to that used with the pigs and in the form of Ca-HMB.

Experimental Procedure

In a controlled double-blind study, the effects of feeding HMB on loss of urinary nitrogen, blood cholesterol and immune function in normal humans were tested. This study also measured blood components that reflect liver, kidney and tissue metabolism. In addition further measurements of nitrogen metabolism and immune function were implemented. All measurements were made in a controlled dietary situation and under blinded conditions. Normal male subjects were used who had been screened for normalcy. Ca-HMB was administered in 250 mg capsules. The subjects were instructed to take the capsules in 4 equal doses daily (with meals and at bed time). The subject ate all their meals under controlled conditions. Normal diets were used, and the amount of the diets was controlled to maintain equal and substantially constant nitrogen intake. The subjects had blood drawn before the morning meal or before they took the morning HMB dose. Each subject was studied twice: once with a placebo and once with HMB. The subjects did not know which preparations they were given, LDL-cholesterol was calculated by the following formula: LDL-cholesterol=(Total Cholesterol) − (HDL-Cholesterol).

Results and Analysis

Plasma HMB in control subjects averaged 1.8 $\mu$M HMB while HMB treated averaged 12 $\beta$M. This increase in plasma HMB produced the results summarized in Table D.

TABLE D

| | Control Group | | Treated Group | | % Change | | % Net |
|---|---|---|---|---|---|---|---|
| | Cont.[a] | Pla[b] | Cont.[a] | HMB[c] | Cont. | Trt. | Effect HMB |
| Weight (lbs.) | 167 | 167 | 176 | 179 | 0 | 1.4 | 1.4 |
| % Body fat (skin fold) | 12.4 | 12.0 | 12.5 | 11.0 | −3 | −12 | −9 |
| Resting metabolic rate | 67.5 | 70.5 | 74.8 | 77.8 | 4 | 4 | 0 |
| Total Cholesterol | 172 | 166 | 187 | 169 | −3 | −10 | −6 |
| HDL Cholesterol | 49.5 | 45.6 | 49.5 | 50.9 | −8 | 3 | 11 |
| LDL Cholesterol | 113 | 118 | 118 | 107 | 2 | −8 | −10 |
| LDL/HDL | 2.28 | 2.58 | 2.38 | 2.10 | 13 | −12 | −25 |

[a] no treatment
[b] placebo treatment with CaCO3 on same dose schedule and Ca level as Ca-HMB treatment
[c] Ca HMB treatment at 1.0 grams/24 hours
[d] % change from control to placebo and control to HMB treatment Body weight, body fat and resting metabolic rate (KCal/mw) did not change with HMB treatment. Consuming 2 g of HMB daily for two weeks reduced total cholesterol 6% and LDL cholesterol 10%, HDL cholesterol increased 11%. The ratio of LDL to HDL decreased 25% in two weeks. Because this study was only two week in duration, the maximum effect obtainable from HMB consumption was probably not obtained. The two week test period was too short. However, this study did show that HMB can effectively decrease LDL cholesterol and favorably charge the LDL/HDL ratio in humans.

TABLE E

| DAILY DOSAGE OF Ca-HMB | | | | | |
|---|---|---|---|---|---|
| | % Change After 8 Days | | | | (PL) Linear |
| | 0.5 g | 1.0 g | 2 g | 4 g | Effect |
| Weight | 1.7 | −.3 | .5 | .2 | .32 |
| Body fat (%) | 5 | −18 | −15 | −1 | NS |
| Glucose | −7 | 2 | −5 | −4 | .99 |
| Cholesterol | 6 | 1 | −2 | −4 | .21 |
| LDL | 2 | 0 | −3 | −6 | .26 |
| HDL | 0 | 6 | 1 | 0 | .85 |
| Triglycerides | 26 | −16 | −8 | 36 | .50 |

EXAMPLE V

Higher dose levels than in Example IV of Ca-HMB were tested in humans. The objective was to obtain an indication of whether higher doses could be safely administered, and also whether higher doses might provide a greater reduction in total cholesterol and LDL cholesterol. The experimental procedure and results obtained are summarized below.

Experimental Procedure

Normal humans were used in the study. Ca-HMB was administered in 250 mg capsules, and the subjects were instructed to take the capsules in 4 equal doses daily. No control of diet was attempted except they were instructed to eat as they normally would. On alternate days the subjects had blood drawn before the morning meal and before they took the morning HMB dose. Four subjects were studied for dose level of 05., 1, 2 and 4 grams per day.

Analysis

Results from all samples of each subject were subjected to linear regression and the slope and intercept used to calculate the % change in concentration after 8 days on treatment. The percentage changes were then subjected to ANOVA-regression to determine if there was a linear effect of dosage on the parameter. The dose-response effect (p<) is listed in the linear effect column of Table E.

Discussion Of Results

Blood HMB increased in a dose-responsive manner. A very large increase in blood HMB occurred at 4 grams per day. This suggests that higher doses than the 1 g per day of Example IV are desirable for maximum cholesterol reduction. In general there were no adverse affects of HMB noted. The only complaint noted with several patients was of being hungrier than normal. Body fat measurements were somewhat limited in this study in that only half the subjects had the measurements. However, the study combined with the study of Example IV is extremely suggestive of an effect on body fat. Over the course of the week, blood cholesterol decreased in a dose-responsive manner as shown in Table E. At an HMB dose of 4 grams per day, total cholesterol and LDL cholesterol decreased about 6% by the end of the one week study. An HMB dose of 2 grams daily also appeared to decrease cholesterol, but at lower doses no effect was clearly observable in this short term study.

I claim:

1. The method of treating a human patient having elevated blood levels of low-density lipoprotein cholesterol and total cholesterol, comprising orally administering to the human patient an effective amount of an edible form of $\beta$-hydroxy-$\beta$-methylbutyric acid for reducing the patient's blood level of said lower density cholesterol and total cholesterol, said edible form consisting of (i) its free acid from, or (ii) its sodium, potassium, or calcium salt, or (iii) its methyl or ethyl ester, or (iv) its lactone, said effective amount being within the range of from 0.01 to 0.20 grams of said edible form per kilogram body weight per 24 hours based on said calcium salt.

2. The method of claim 1 in which said edible form is its calcium salt.

3. The method of claims 1 or 2 in which said effective amount of said edible form is from 0.01 to 0.20 grams per kilogram body weight per 24 hours based on its calcium salt.

4. The method of treating a human patient having an elevated blood level of low-density lipoprotein cholesterol and total cholesterol, comprising orally administering to the human subject an edible form of $\beta$-hydroxy-$\beta$-methylbutyric acid to reduce the patient's blood level of said low density cholesterol and total cholesterol, said edible form consisting of (i) its free acid form, or (ii) its sodium, potassium, magnesium, or calcium salt, or (iii) its methyl or ethyl ester, or (iv) its lactone said edible form being administered in an effective amount within the range from 0.5 to 10 grams per 24 hours based on said calcium salt.

5. The method of claim 5 in which said HMB is in the form of its calcium salt (Ca-HMB).

6. The method of claim 4 or claim 5 in which said HMB (Ca-HMB basis) is administered to the human patient in an amount of from 2 to 6 grams per 24 hours.

* * * * *

UNITED STATES PATENT AND TRADEMARK OFFICE
CERTIFICATE OF CORRECTION

PATENT NO. : 5,360,613

DATED : November 1, 1994

INVENTOR(S) : Nissen

It is certified that error appears in the above-indentified patent and that said Letters Patent is hereby corrected as shown below:

In column 10, line 35, claim 5, delete "claim 5" and insert — claim 4 —.

Signed and Sealed this

Seventh Day of February, 1995

Attest:

BRUCE LEHMAN

*Attesting Officer*    *Commissioner of Patents and Trademarks*